United States Patent
Bastia et al.

(10) Patent No.: US 9,345,747 B2
(45) Date of Patent: May 24, 2016

(54) COMPOSITION AND USE THEREOF IN THE TREATMENT OF ANAL RHAGADES

(75) Inventors: Filippo Bastia, Sozzigalli di Soliera (IT); Maurizio Saccomanno, Gallipoli (IT)

(73) Assignee: THD, Correggio, RE (IT)

(*) Notice: Subject to any disclaimer, the term of this patent is extended or adjusted under 35 U.S.C. 154(b) by 0 days.

(21) Appl. No.: 14/359,504

(22) PCT Filed: Jan. 30, 2012

(86) PCT No.: PCT/IT2012/000027
§ 371 (c)(1),
(2), (4) Date: May 20, 2014

(87) PCT Pub. No.: WO2013/114410
PCT Pub. Date: Aug. 8, 2013

(65) Prior Publication Data
US 2014/0303094 A1    Oct. 9, 2014

(51) Int. Cl.
*A61K 36/18*   (2006.01)
*A61K 38/16*   (2006.01)
*A61K 31/716*  (2006.01)
*A61K 36/185*  (2006.01)
*A61K 9/00*    (2006.01)
*A61K 47/10*   (2006.01)
*A61K 47/36*   (2006.01)
*A61K 38/01*   (2006.01)

(52) U.S. Cl.
CPC ............ *A61K 38/168* (2013.01); *A61K 9/0031* (2013.01); *A61K 31/716* (2013.01); *A61K 36/185* (2013.01); *A61K 38/011* (2013.01); *A61K 47/10* (2013.01); *A61K 47/36* (2013.01)

(58) Field of Classification Search
CPC .......................... A61K 36/18; A61K 31/7165
USPC ........................................................... 424/776
See application file for complete search history.

(56) References Cited

U.S. PATENT DOCUMENTS

| 6,956,120 B2* | 10/2005 | Ikewaki et al. ............ 536/123.12 |
| 2006/0093657 A1* | 5/2006 | Pinna ................... A61K 9/7053 424/448 |
| 2009/0202664 A1* | 8/2009 | Mikalacki et al. ............ 424/730 |
| 2011/0305744 A1* | 12/2011 | Russo .................. A61K 9/0031 424/430 |

FOREIGN PATENT DOCUMENTS

| FR | WO 9846205 A1 * | 10/1998 | ............. A61K 8/068 |
| WO | 98/46205 A1 | 10/1998 | |

OTHER PUBLICATIONS

Mathur, J.M.S. (Current Science 1968,vol. 37(2), 54-5).*
"Anal Fissure/Colorrectal Surgery" Univerisy Hospitals, Case Medical Center, http,http;uhhospitals.org Aug. 6, 2014.*
International Search Report of PCT/IT2012/000027.
Database WIPI XP002681035 & JP 2004 051533 A Feb. 19, 2004.
Bryant et al: Processing, Functional, and Nutritional Properties of Okra Seed Products Journal of Food Science, vol. 53, No. 3, pp. 810-816 Jan. 1, 1988.

* cited by examiner

*Primary Examiner* — Chris R Tate
*Assistant Examiner* — Deborah Davis
(74) *Attorney, Agent, or Firm* — Silvia Salvadori, P.C.; Silvia Salvadori

(57) ABSTRACT

The present invention relates to a composition comprising at least one protein extract of hibiscus and/or at least one beta glucan or a salt thereof. Furthermore, the present invention relates to the use of said composition for the treatment of anal rhagades.

23 Claims, No Drawings

COMPOSITION AND USE THEREOF IN THE TREATMENT OF ANAL RHAGADES

This application is a U.S. national stage of PCT/IT2012/000027 filed on Jan. 30, 2012, the content of which is incorporated herein by reference in its entirety.

The present invention relates to a composition comprising at least one protein extract of hibiscus and/or at least one beta glucan. Furthermore, the present invention relates to the use of said composition for the treatment of anal rhagades.

An anal rhagade is an ulceration of the epithelium of the lower anal canal, usually located at the level of the posterior commissure of the canal and accompanied by a contracture of the internal sphincter. The laceration of the anal mucosa at the site of the rhagade provokes light bleeding, which occurs during defecation. The condition of internal sphincter contracture results in anal canal hypertony, which is the cause of pain (dominant symptom). The pain is so intense and acute, especially during and after defecation (up to 3-4 hours), as to induce the subject to avoid defecating, the consequence being a possible hardening of the faeces and, therefore, exacerbation of the problem.

An anal rhagade can occur in individuals of various age with no difference between the sexes; however, it has been experimentally demonstrated that individuals of 20-40 years of age are most exposed to risk. Anal rhagades represent the second most common cause leading to a proctological examination after a haemorrhoidal pathology; in fact, the frequency of anal rhagades in a proctology outpatient clinic is 9-12%. According to data in the 2009 Annual Report of the SICCR (Italian Society of Colorectal Surgery), a total of 5199 cases of anal rhagades were observed and 37% of the patients (1924) underwent surgery.

Even though the clinical manifestations of rhagades are well known, their ethiopathogenesis still remains unclear.

According to the mechanical theory, the triggering factor is often represented by a laborious defecation and the trauma due to the passage of hard faeces. This causes a strong, persistent pain, which induces the individual to suppress the stimulus and put it off, causing a further hardening of the faeces and worsening of the condition.

It is thus possible that a traumatic factor provokes the rhagades, which would heal, however, if other factors did not intervene. The first of these is the presence of a persistent hypertony of the internal anal sphincter, and the second is a condition of localised ischemia at the level of the anal canal. In fact, the anal canal, where the rhagades are located, is supplied blood by the inferior rectal artery. However, in 85% of individuals with rhagades it is possible to observe (by angiography) a relative arterial deficiency at the level of the posterior commissure of the anal canal. Moreover, the blood flow diminishes with increasing anal pressure and vice versa. Therefore, the hypertony and ischemia are closely correlated phenomena. Anal rhagades can be distinguished into an acute and a chronic form.

The acute form is a superficial radial lesion of the anoderm (i.e. the epithelial lining of the anal canal), characterized by smooth edges and a rose-coloured background. It is usually associated with very severe pain. The acute form can tend toward cicatrisation, but frequently relapses or evolves into the chronic form. A rhagade is considered acute when it is present for less than 6 weeks. Spontaneous healing of acute anal rhagades occurs in 70% of the cases.

The therapeutic treatment for an acute rhagade is of a conservative type; in fact, surgery is performed only in the event of therapeutic failure.

A chronic anal rhagade is a deep radial lesion of the anoderm, characterized by raised whitish edges with fibres of the smooth sphincter visible in the background. It is often accompanied by the presence of a hypertrophic anal papilla, that is to say, a small soft protrusion of the anal canal epithelium. A rhagade is considered chronic when it is present for more than 6 weeks. Chronic rhagades usually heal spontaneously in only 20% of cases at most.

In light of the fact that chronic anal rhagades have a very low percentage of healing, a great deal of research has been conducted with the aim of identifying new increasingly better therapeutic approaches, be they of a conservative or surgical type.

Acute anal rhagades can be healed in a conservative manner also by eliminating the spasm of the internal sphincter responsible for the hypertony.

The conservative therapy suggests a diet rich in roughage and an abundant intake of liquids as well as very thorough, delicate local hygiene. When rhagades are associated with constipation it is recommended to use lubricants, and/or fibres to render the faeces softer.

The medical therapeutic approach pursues the objective of reducing the hypertony of the internal anal sphincter so as to facilitate healing of the rhagades.

Recent studies on the physiopathology of the anal sphincter have demonstrated that nitric oxide is an inhibitor of internal anal sphincter tone. Therefore, a so-called "reversible chemical sphincterotomy" can be performed by locally applying an ointment based on trinitroglycerin (TNG), which is capable of bringing about a relaxation of the internal anal sphincter. An average healing of 58% of cases within two months of treatment has been demonstrated, with relapses occurring in 11 to 46.2% of the cases.

The most frequent complication of this treatment is headache, which occurs in 57% of the cases on average and sometimes requires the treatment to be interrupted. Alternatively, the medical therapy for rhagades proposes injecting botulinum toxin into the smooth internal sphincter in order to heal them by bringing about a reduction in internal anal sphincter tone. Usually, a few hours after administration of the toxin a flaccid paralysis occurs which tends to persist for 3-4 months.

Cicatrisation of rhagades occurs within two months after the treatment in 2-96% of the cases, with relapses in 30% of the cases.

However, in 18% of the cases this treatment manifests a highly disabling side effect, i.e. temporary faecal incontinence.

A further therapeutic alternative provides for the administration of calcium channel blockers. These bring about a lowering in the maximum sphincter pressure at rest, with serious overdose side effects in the cardiopathic and diabetic patients.

When satisfactory responses are not obtained with conservative or pharmaceutical therapeutic treatments, or if the rhagades recur and worsen over time, surgical treatment becomes necessary; this may involve various techniques that are invasive to a greater or lesser degree. A "modern" version of anal divulsion (by now considered obsolete), defined as "mechanical anal sphincteroclasia", can be performed. This technique provides for the use of a rubber balloon, which is inserted into the anal canal and inflated at a controlled pressure. The internal sphincter is thereby dilated for a few minutes (approximately 5) and the sphincter hypertony is overcome. A negative event can be the onset of faecal incontinence of varying degrees, also persistent, in a considerable percentage of cases (8-35%).

The "gold standard" treatment for anal rhagades is "lateral internal sphincterotomy". It is defined "open" when it provides for a skin incision with exposure of the sphincter, and it is defined "closed" when performed transcutaneously without exposure of the sphincter.

Both techniques are capable of guaranteeing healing in a high percentage of patients (over 90% of cases heal within 2 months after the treatment).

The most serious complication is faecal incontinence, which in the majority of cases is transitory (8.9%-13.00 of cases), but in some cases can become persistent (0.6% -6.9%).

The surgery can also be modulated with a "regulated lateral internal sphincterotomy", which allows the entity of the section to be incised to be regulated based on the extent of the rhagade, length of the sphincter and degree of hypertony measured. This serves to reduce the cases of failure due to persistence or relapsing of the rhagade and the complications related to incontinence.

Given the widespread nature of this pathological condition, most of the times associated with very severe, disabling pain, there is still a strongly felt need for new therapeutic approaches capable of healing anal rhagades or at least alleviating the pain thereof. In particular, clinical research in this field always focuses a great deal of attention on identifying new therapies of a conservative type, e.g. pharmacological protocols, so as to reduce the need for surgery, which, as previously described, is capable of healing anal rhagades, but often causes incontinence, which is a non-physiological condition that is equally disabling for an individual, especially from psychological-social point of view.

The present invention fits into this context and relates to a composition comprising at least one protein extract of hibiscus and at least one beta glucan or a salt thereof, as described in the appended claims.

Furthermore, the present invention relates to the use of a composition comprising at least one protein extract of hibiscus and/or at least one beta glucan or a salt thereof for the treatment of anal rhagades, as described in the appended claims.

In fact, the Applicant has surprisingly found that the application of a composition comprising one protein extract of hibiscus and/or one beta glucan on anal rhagades is capable of improving a symptomatic or asymptomatic condition caused by anal rhagades right from the very first applications.

In particular, the Applicant has found that this composition is capable of alleviating the pain associated with defecation by exerting a reparatory action on the local epithelium and likewise a reduction in the hypertony of the internal sphincter, thus favouring relaxation of the smooth muscle of the anal canal.

A first aspect of the present invention relates to the at least one protein extract of hibiscus, which is preferably a protein extract of Hybiscus esculentus, otherwise known as okra or Abelmoschus esculentus, that is, a plant belonging to the family Malvaceae, which generally grows in tropical regions.

Said at least one protein extract of hibiscus is preferably at least one protein fraction, more preferably at least one soluble protein fraction, originating, preferably, from hibiscus seeds. In particular, the protein extract derives from hibiscus seeds, preferably a meal of hibiscus seeds, more preferably delipidated seeds and/or meal.

Said protein extract or said protein fraction is preferably a protein hydrolysate obtainable, preferably, from the native protein. The hydrolysate can be obtained by enzymatic hydrolysis and/or chemical hydrolysis. Alternatively, the hydrolysate is obtained by biotransformation.

In the context of the present invention biotransformation means a process able to render a substance more hydrosoluble, for example by functionalizing it by hydrolysis, oxidation, reduction or conjugation, so as to introduce or expose the hydrophilic groups.

In some embodiments said hydrolysate is a mixture of oligopeptides. Preferably said hydrolysate is in a mixture with a binder, more preferably with a dextrin. In preferred embodiments, the ratio between said hydrolysate and said binder is preferably 1:1. The mixture of oligopeptides preferred for the purposes of the present invention is the commercial product with the Myoxinol™ trademark.

The concentration of said at least one protein extract of hibiscus ranges between 0.1 and 10%; it preferably ranges between 0.4 and 5%.

A second aspect of the present invention relates to the beta glucan, which is preferably carboxymethyl beta-glucan and/or a salt thereof, more preferably sodium carboxymethyl beta-glucan.

The concentration of said beta glucan ranges between 0.004 and 0.4%; it preferably ranges between 0.02 and 0.08%.

The ratio between said at least one protein extract of hibiscus and said at least one beta glucan is preferably 50-10:1, more preferably 35-20:1. The composition of the present invention is characterized by a pH that preferably ranges from 5 to 8; more preferably it ranges between 5.5 and 6.5. For the purpose of adjusting the pH of the composition of the invention, a pH regulating agent (which we will define as pH adjuster) can be used, preferably a basic substance, for example triethanolamine.

The concentration of said agent ranges between 0.03 and 1%; it preferably ranges between 0.1 and 0.6%.

In preferred embodiments, the composition of the invention, preferably formulated as a gel cream (i.e. gel emulsion), is characterized by a viscosity that preferably ranges between 5000 and 30000; more preferably it ranges between 7000 and 25000 (meas).

The composition of the present invention may further comprise at least one pharmacologically acceptable excipient, or a compound acceptable per pharmaceutical use or for cosmetic use, which is useful in preparing the composition and is generally biologically safe and non toxic.

Said excipient can be at least one conditioning agent, preferably a moisturizing, occlusive or emollient conditioning agent for the skin or hair.

In particular, said conditioning agent is selected in the group consisting in: dimethicone or dimethyl polysiloxane, preferably linear, glycerine, almond oil (preferably Prunus amygdalus dulcis oil), phenyl trimethicone, borage oil (preferably oil from the seeds of Borago officinalis), malva extract and/or mucilage, preferably mucilage of Malva sylvetris, panthenol, extract of calendula, preferably of Calendula officinalis, ethylhexylglycerin, caprylyl glycol, aspartic acid, maltodextrins and glyceryl stearate.

The concentration of said conditioning agent ranges preferably between 15 and 35%, preferably between 20 and 25%.

Preferably, the concentration of said dimethicone or dimethyl polysiloxane ranges between 2.5 and 10%; more preferably it ranges between 3.5 and 7%. Preferably, the concentration of said glycerine ranges between 2.5 and 10%; more preferably it ranges between 3.5 and 7%.

Preferably, the concentration of said almond oil ranges between 2 and 8%; more preferably it ranges between 3 and 6%.

Preferably, the concentration of said phenyl trimethicone ranges between 1 and 4%; more preferably it ranges between 1.5 and 3%.

Preferably, the concentration of said borage oil ranges between 1 and 4%; more preferably it ranges between 1.5 and 3%.

Preferably, the concentration of said malva extract ranges between 1 and 4%; more preferably it ranges between 1.5 and 3%.

Preferably, the concentration of said panthenol ranges between 0.5 and 2%; more preferably it ranges between 0.75 and 1.5%.

Preferably, the concentration of said calendula extract ranges between 0.1 and 0.4%; more preferably it ranges between 0.15 and 0.3%.

Preferably, the concentration of said caprylyl glycol ranges between.0.1 and 0.4%; more preferably it ranges between 0.15 and 0.3%.

Preferably, the concentration of said maltodextrins ranges between 0.1 and 0.4%; more preferably it ranges between 0.15 and 0.3%.

Preferably, the concentration of said glyceryl stearate ranges between 0.4 and 1.8%; more preferably it ranges between 0.5 and 1.2%.

Preferably, the concentration of said ethylhexylglycerin ranges between 0.05 and 0.2%; more preferably it ranges between 0.75 and 0.15%.

Preferably, the concentration of said aspartic acid ranges between 0.0002 and 0.001%; more preferably it ranges between 0.0003 and 0.0008%.

Said excipient can additionally be a surfactant, preferably an emulsifying or cleaning surfactant. More preferably, said surfactant is selected in the group consisting of: cetyl alcohol, cetyl(20) OE or ceteth-20, stearyl(20)0E or steareth-20 and PEG-75 stearate. The concentration of said surfactant preferably ranges between 1 and 3%; more preferably it ranges between 1.2 and 2%.

The concentration of said cetyl alcohol ranges preferably between 0.5 and 1%; or the concentration of said PEG-75 stearate preferably ranges between 0.2 and 1%; or the concentration of said ceteth-20 or said steareth-20 preferably ranges between 0.05 and 0.25%. Additionally, said excipient can be a preservative, preferably phenoxyethanol; or else said excipient can be an antioxidant, preferably selected between tocopherol and liquorice (glycyrrhiza glabra) dry extract.

The concentration of said preservative preferably ranges between 0.3 and 1%, more preferably between 0.5 and 1%; the concentration of said antioxidant preferably ranges between 0.1 and 1%, more preferably between 0.2 and 0.6%.

Said excipient can additionally be a binder, preferably selected from among the dextrins; or else said excipient can be a stabilizing agent, preferably an emulsifying stabilizing agent, more preferably a crosslinked acrylic copolymer; or else said excipient can be a chelating agent, preferably trisodium ethylenediamine disuccinate. Preferably, the concentration of said binder ranges between 0.5 and 2%, more preferably between 0.75 and 1.5%; the concentration of said chelating agent preferably ranges between 0.01 and 0.08%, more preferably between 0.02 and 0.06%; and the concentration of said stabilizing agent preferably ranges between 0.15 and 0.6%, more preferably between 0.2 and 0.4%. The percentages given above for the concentration of the various components of the composition of the invention are to be considered as weight/weight percentages, and thus refer to 100 grams of product. The composition of the present invention is produced in a solvent, which is water and/or 1,2-hexanediol. With said solvent, the composition is brought to 100% of its final weight.

A further aspect of the present invention relates to the composition of the invention formulated for topical use, in particular, formulated as a cream, gel cream, gel, oil, emulsion, gel emulsion (emulgel) ointment, spray or suppository or stick (like a cocoa butter stick).

Alternatively, the composition of the present invention can be formulated for oral use, preferably as a lozenge, tablet or granules, or for injectable use.

The composition can be formulated to release the active principles contained therein rapidly, or in a delayed and/or controlled manner after administration.

A further aspect of the present invention relates to the use of a composition comprising at least one hibiscus extract and at least one beta glucan or a salt thereof as a medication.

A further aspect of the present invention relates to the use of a composition comprising at least one hibiscus extract and/or at least one beta glucan or a salt thereof for the treatment of anal rhagades, preferably acute anal rhagades.

In a preferred embodiment, the composition of the invention is administered topically, preferably at least once a day, more preferably at least twice a day. Administration is preferably carried out for a period of at least one week, more preferably for at least two weeks. The best results are obtained with a treatment of at least twenty days.

The composition of the present invention can be administered on its own or in combination with additional agents which are effective or adjuvant in the treatment of rhagades.

Alternatively the composition can be used in association with other methods and/or protocols for treating anal rhagades. Preferred examples of said methods and/or protocols regard the use of anal dilators.

A further aspect of the present invention relates to a method for producing a composition comprising at least one protein extract of hibiscus and/or at least one beta glucan according to the present invention. Said method comprises the following steps:

(i) melting the conditioning agents, preferably the occlusive and/or emollient conditioning agents, and/or the surfactants, preferably the emulsifying and/or cleaning surfactants, at a temperature that ranges between 70 and 90° C.; more preferably it ranges between 75 and 80° C.;

(ii) mixing the solvent, the conditioning agents, preferably moisturizing ones, the chelating agents and/or the stabilizing emulsifying agents with the raw materials melted according to step (i);

(iii) adding at least one hibiscus extract to the mixture according to step (ii);

(iv) adding at least one beta glucan to the mixture according to step (iii).

Said hibiscus extract according to step (iii) is solubilized, preferably in water, and more preferably in purified water. Solubilization is achieved at a temperature that preferably ranges between 40 and 60° C.; more preferably it ranges between 50 and 55° C. Said at least one beta glucan according to step (iv) is preferably added as a 1-5% aqueous solution (the percentage is a weight/weight percentage), more preferably 1.5-2.5%. The temperature of the mixture to which said at least one beta glucan is added preferably ranges between 35 and 45° C., more preferably between 32 and 37° C.

The mixing of the components of the composition of the invention preferably continues until a semi-processed product is obtained. Said semi-processed product can be ready for use or for packaging.

A further aspect of the present invention relates to a kit comprising a composition comprising at least one protein extract of hibiscus and/or at least one beta glucan or a salt thereof.

Preferably, the composition of the kit is formulated as a cream, gel or emulsion gel. More preferably the kit comprises at least one, preferably at least twenty dispensers (for example squeeze tubes) containing the composition of the invention, preferably in a pre-dosed amount. The dispensers are preferably single-use and, more preferably, are provided with an applicator which is preferably incorporated in said dispenser for the purpose of facilitating the application of the composition on the rhagade to be treated.

Preferably, the dispensers are dimensioned in such a way as to deliver, on application, the pre-dosed, sufficient, necessary amount of the composition.

EXAMPLE

Method of producing the composition according to the present invention in the form of a gel cream.

Introduce the raw materials into the mixer according to the procedure and amounts provided for in the formula. The raw materials requiring a melting process before being mixed with the other ingredients of the formula are melted in the melting unit at a temperature that ranges from 75-80° C.

Subsequently, the temperature of the mixture is lowered to 50-55° C. and the Myoxinol solubilized in hot purified water (50-55° C.) is added and the beta glucan (2% solution) is subsequently added together with the other components that do not require melting or solubilization. These ingredients are added to the mixture at a temperature below 35° C. and the mixing continues until a semi-processed product ready for use/packaging is obtained.

Formulation Examples

An example of the composition of the invention formulated as a gel/cream and functioning for the purposes of the claimed uses is given below in Table 1.

TABLE 1

| INCI EU | % |
| --- | --- |
| Purified water | q.s. to 100 |
| Glycerine | 5.0000% |
| Dimethyl polysiloxane | 5.0000% |
| Sweet almond oil (*Prunus dolcis*) | 4.0000% |
| *Malva* mucilage (*Malva sylvestris*) | 2.0000% |
| Borage oil (*Borago officinalis*) | 2.0000% |
| Phenyl trimethicone | 2.0000% |
| d-panthenol | 1.0000% |
| Dextrin | 0.8625% |
| Hydrolyzed hibiscus extract | 0.8625% |
| Cetyl alcohol | 0.8625% |
| Glyceryl stearate | 0.8625% |
| Phenoxyethanol | 0.5000% |
| Stearate (75) OE | 0.4250% |
| Crosslinked acrylic copolymer | 0.3000% |
| Triethanolamine | 0.3000% |
| Calendula dry extract | 0.2000% |
| Liquorice dry extract | 0.2000% |
| Cetyl (20) OE | 0.1750% |
| Stearyl (20) OE | 0.1750% |
| Tocopherol | 0.1000% |
| Ethylhexylglycerin | 0.0800% |
| Carboxymethyl beta-glucan sodium salt | 0.0300% |

Rectal Mucosa Irritation Test of with the Composition of the Invention.

The composition of the invention in the form of a gel cream was subjected to a rectal mucosa irritation test.

The test was performed on 6 male albino rabbits. In particular, 3 rabbits were treated with 1 ml of the gel/cream composition, 3 rabbits were treated with 1 ml of saline solution (controls). The treatment provides for the gel/cream (treated samples) or saline solution (control samples) to be introduced directly into the rectum of each animal using a soft catheter. This treatment was repeated for 5 consecutive days. The rectal mucosa of each animal was observed daily for the purpose of detecting any irritation phenomenon, for example erythema and/or the presence of scabs. Twenty-four hours after the last day of treatment, the animals were sacrificed and a sample was taken of the rectal mucosa of the animals for the purpose of performing a histological examination.

The microscopic reactions detected were evaluated on the basis of the data shown in Table 3.

TABLE 3

| Reaction | Numerical classification |
| --- | --- |
| 1. Epithelium | |
| Normal, intact | 0 |
| Cell degeneration or flattening | 1 |
| Metaplasia | 2 |
| Focal erosion | 3 |
| Generalized erosion | 4 |
| 2. Infiltration of leukocytes (for high power field) | |
| Absent | 0 |
| Minimal (less than 25) | 1 |
| Slight (from 26 to 50) | 2 |
| Moderate (from 51 to 100) | 3 |
| Marked (greater than 100) | 4 |
| 3. Vascular congestion | |
| Absent | 0 |
| Minimal | 1 |
| Slight | 2 |
| Moderate | 3 |
| Marked, with vessel rupture | 4 |
| 4. Oedema | |
| Absent | 0 |
| Minimal | 1 |
| Slight | 2 |
| Moderate | 3 |
| Marked | 4 |

In the macroscopic examination, the inflammatory reactions detected in the area of application of the animals treated with the test composition are compared with those detected in the control animals.

The scores of the microscopic evaluations of all the animals treated with the test composition are added together and divided by the number of animals to obtain the average irritative potential for the treated group. The same calculation is performed for the control group.

A score of 9 in the microscopic evaluation of control tissues may indicate an underlying pathology or, in a control animal, it may indicate a trauma due to administration. Both situations may require a retest if other animals in the test or control group display the same high scores. The control group average is subtracted from the test group average to obtain the irritation index.

The irritation indices are shown in Table 4.

TABLE 4

IRRITATION INDEX

| AVERAGE SCORE | DESCRIPTION |
| --- | --- |
| 0 | None |
| 1-4 | Minimal |
| 5-8 | Slight |
| 9-11 | Moderate |
| 12-16 | Severe |

The results of the macroscopic evaluation are shown in Table 5.

TABLE 5

| Treated rabbit No | | | |
| --- | --- | --- | --- |
| 1199 | 1200 | 1201 | Average (x) |
| 0 | 0 | 0 | 0.00 |
| 0 | 0 | 0 | 0.00 |
| 0 | 0 | 0 | 0.00 |
| Control rabbit No | | | |
| 1202 | 1203 | 1204 | Average (x) |
| 0 | 0 | 0 | 0.00 |
| 0 | 0 | 0 | 0.00 |
| 0 | 0 | 0 | 0.00 |

No anomaly due to treatment with the test composition or with the saline solution was detected in the animals.

The microscopic results are summed up in Table 6.

TABLE 6

| | Treated rabbit No | | |
| --- | --- | --- | --- |
| Parameters | 1199 | 1200 | 1201 |
| Epithelium | 0 | 0 | 0 |
| Leukocyte infiltration | 0 | 0 | 0 |
| Vascular congestion | 0 | 0 | 0 |
| Oedema | 0 | 0 | 0 |
| | Control rabbit No | | |
| Parameters | 1202 | 1203 | 1204 |
| Epithelium | 0 | 0 | 0 |
| Leukocyte infiltration | 0 | 0 | 0 |
| Vascular congestion | 0 | 0 | 0 |
| Oedema | 0 | 0 | 0 |

Based on the results shown in Table 6, the composition according to the present invention displays an irritative potential equal to zero. The rectal irritation index is indeed zero.

In conclusion, the composition of the present invention can be considered non-irritating to the rectal mucosa. Delayed hypersensitivity test - Guinea pig maximization test (GPMT) with the composition of the invention. The test was performed on white female guinea pigs; in particular, a group of 10 animals (group 1) was treated with the composition of the invention, whereas 5 animals formed the control group (group 2).

Group 1 was treated with the composition in the form of a gel/cream, whereas group 2 was treated with a saline solution.

Group 1 was treated with a 1-50:50 (v:v) intradermal injection (sample 1) of a stable emulsion of Freund's complete adjuvant (ECA) with saline solution and the product being tested diluted 50:50 (v:v) with a stable emulsion of FCA and saline solution (50%).

The animals in group 2 were treated with a 1-50:50 (v:v) intradermal injection (sample 2) of a stable emulsion of Freund's complete adjuvant (FCA) with saline solution. The saline solution was diluted 50:50 (v:v) with a stable emulsion of FCA and saline solution (50%). The animals used in the study were randomly selected among the suitable animals available at the time of the study. The animals were divided into groups, with a maximum of 5 animals per cage.

Twenty-four hours prior to treatment an area of about 50 $cm^2$ was shaved on the animals' back. The test consists in an induction phase and a challenge phase.

During the induction phase on day zero (0), three pairs of intradermal injections, each containing 0.1 ml of the sample described above, were performed on all animals on either side of the median line, in the subscapular areas.

On day six of the induction phase, after the intradermal injections, 1 ml of 10% sodium lauryl sulphate was topically applied, through a gentle massage, on all animals.

On day 7 of the induction phase, after the intradermal injections, 1 ml of the sample was topically applied under an occlusive dressing on all animals. The application was applied randomly in relation to the injection site.

The dressing was left on for 48 hours. The same treatment was performed on the control group using saline solution instead of the composition of the invention.

As regards the challenge phase, on the twenty-first day all of the guinea pigs were topically treated under an occlusive dressing on the right flank with 1 ml of the composition tested and diluted as described above. The dressing was left on for 24 hours.

On the twenty-third day (24 hours after removal of the dressing) and on the twenty-fourth day (48 hours after removal of the dressing), the skin reactions in all animals were evaluated. The intensity of erythema and oedema were evaluated according to the Magnusson and Kligman scale as shown in Table 7.

TABLE 7

| Reaction | Numerical scale |
| --- | --- |
| No visible change | 0 |
| Discrete or patchy erythema | 1 |
| Moderate and confluent erythema | 2 |
| Intense erythema and swelling | 3 |

Magnusson and Kligman scale values greater than or equal to 1 in the test group generally indicate sensitization, provided that values of less than 1 have been observed in the control animals.

If values greater than or equal to 1 are observed in the control animals, it may be assumed that the reactions in the test animals that exceed the most severe reaction of the control animals are due to sensitization.

If the response is ambiguous, it is necessary to carry out a rechallenge to confirm the results of the first challenge. The test outcome is presented as the frequency of positive responses to the challenge in the test and control animals.

The results are summarized in Table 8.

TABLE 8

| Animals treated with the composition | Time since removal of dressing | |
|---|---|---|
| | 24 hours | 48 ore hours |
| 1 | 0 | 0 |
| 2 | 0 | 0 |
| 3 | 0 | 0 |
| 4 | 0 | 0 |
| 5 | 0 | 0 |
| 6 | 0 | 0 |
| 7 | 0 | 0 |
| 8 | 0 | 0 |
| 9 | 0 | 0 |
| 10 | 0 | 0 |

| Control animals | Time since removal of dressing | |
|---|---|---|
| | 24 hours | 48 hours |
| 1 | 0 | 0 |
| 2 | 0 | 0 |
| 3 | 0 | 0 |
| 4 | 0 | 0 |
| 5 | 0 | 0 |

The results demonstrate that nothing abnormal was detected either in the animals treated with the present composition or in the control animals and that the percentage of sensitized guinea pigs is thus equal to zero (0).

First study on subjects affected by anal rhagades and treated with the composition of the present invention.

Ten subjects with acute anal rhagades, aged 21 to 72 years (mean age 38.7 years), underwent treatment with the composition of the invention. The treatment lasted for one month and was carried out by topically treating the rhagade with the composition in gel cream form three times a day.

The subjects did not report any type of side effect. After the month of treatment, there was a complete remission of painful symptoms in 5 out of 10 subjects, whereas a significant reduction in the same was observed in another 4 subjects. Pain was measured using the Visual Analogue Scale (VAS) and the mean VAS ranged from 9 to 3.25.

In 6 out of 10 subjects, complete cicatrisation of the rhagade was ascertained after one month of treatment. At the end of the topical treatment, a further dilating treatment was necessary in 7 subjects, by whom it was well accepted considering the fact that the treated subjects had seen a distinct improvement in their symptoms.

At the second examination, performed after 60 days, complete cicatrisation was observed in 9 out of 10 subjects.

The only subject who had not healed completely continued with a dilating treatment for an additional twenty days and showed to have healed completely at the next examination (i.e. 90 days after the start of the treatment).

Second study on subjects affected by anal rhagades and treated with the composition of the present invention. Ten subjects with acute anal rhagades were treated with the composition of the invention in gel cream form. The treatment was performed with doses of 3 grams/day for 30 days or 3 grams/day for 50 days.

The subjects underwent anoscopy on an outpatient basis to arrive at a diagnosis of anal rhagades.

The subjects were instructed on how to apply the gel cream- and- the event of concomitant constipation, a therapy based on faecal emollients was administered (FIBRAID, one sachet twice a day) for 30 or 50 days respectively.

A clinical follow up, consisting in an examination and anoscopy, was performed at 10 and 30 days.

The primary end point was resolution of the symptoms reported during the first examination.

The secondary end point was macroscopic resolution of the rhagade.

The characteristics of the subjects and the results evaluated in the follow up are summarized in Table 9.

Constipation was a condition present in approximately 70% of the subjects.

58% of the treated subjects observed an immediate benefit, with resolution or a distinct improvement of the symptoms as early as 10 days after the treatment; the percentage increased to 75% at 30 days.

Macroscopic resolution of the rhagade occurred in two subjects after 10 days—in the subjects treated within one month of the onset of symptoms.

At 30 days, resolution of the rhagade was observed in over 50% of the subjects.

The total rate of need for further treatment was 27%, with one subject lost to follow-up at 50 days.

No adverse events or complications were reported by the subjects in the various follow-up periods.

TABLE 9

| Subject N. | Duration of Symptoms up to diagnosis | Associated constipation | Associated diarrhoea | Resolution of symptoms 10 d | Resolution of rhagade 10 d | Resolution of symptoms 30 d | Resolution of rhagade 30 d | Need for other therapy |
|---|---|---|---|---|---|---|---|---|
| 1 | 1 month | + | − | + | − | + | + | − |
| 2 | 15 days | + | − | + | − | + | + | − |
| 3 | 3 months | + | − | − | − | + | − | − |
| 4 | 1 month | − | − | + | − | + | + | − |
| 5 | 20 days | + | − | + | − | + | + | − |
| 6 | 3 months | + | − | − | − | − | − | + |
| 7 | 4 months | − | + | − | − | − | − | + |
| 8 | 15 days | + | − | + | − | + | + | − |
| 9 | 1 month | − | − | + | + | + | + | − |
| 10 | 7 days | + | − | + | − | + | + | − |

The invention claimed is:

1. A method for treating anal rhagades in a patient in need thereof comprising topically administering to said patient a medicament containing an effective amount of at least one protein extract of *Hibiscus*, wherein said at least one protein extract is a protein hydrolysate.

2. The method according to claim 1, wherein the anal rhagades are of an acute and/or chronic type.

3. The method according to 1, wherein said administering is in association with a method and/or protocol for treating anal rhagades.

4. The method according to claim 1, wherein said *Hibiscus* is *Hibiscus esculentus*.

5. The method according to claim 1, wherein said protein extract is obtained from the seeds of said *hibiscus*.

6. The method according to claim 5, wherein said seeds are delipidated.

7. The method according to claim 1, wherein said at least one protein extract is a protein fraction.

8. The method according to claim 7, wherein said protein fraction is a soluble protein fraction.

9. The method according to claim 1, wherein said hydrolysate contains a mixture of oligopeptides, and wherein said hydrolysate is combined with a binder.

10. The method according to claim 1, wherein said protein extract of hibiscus is present in a concentration that ranges between 0.1 and 10%.

11. The method according to claim 1, wherein the composition further comprises at least one beta glucan or a salt thereof.

12. The method according to claim 11, wherein said at least one beta glucan is carboxymethyl-beta glucan.

13. The method according to claim 11, wherein said at least one salt of beta glucan is sodium carboxymethyl-beta glucan.

14. The method according to claim 11, wherein said beta glucan is present in a concentration that ranges between 0.004 and 0.4%.

15. The method according to claim 11, wherein the ratio between said at least one protein extract and said at least one beta glucan is 10-50: 1.

16. The method according to claim 1, wherein said composition further comprises a conditioning agent selected from the group consisting of dimethicone or dimethyl polysiloxane, glycerine, almond oil, phenyl trimethicone, borage oil, malva extract and/or mucilage, panthenol, extract of calendula, ethylhexylglycerin, caprylyl glycol, aspartic acid, maltodextrins and glyceryl stearate.

17. The method according to claim 1, wherein said composition further comprises a surfactant selected from the group consisting of cetyl alcohol, cetyl (20) OE or ceteth-20, stearyl (20) OE or steareth-20 and PEG-75 stearate.

18. The method according to claim 1, wherein said composition further comprises a preservative, an antioxidant, a liquorice dry extract, a binder, a stabilizing agent or a chelating agent.

19. The method according to claim 1, wherein said composition is formulated as cream, gel cream, gel, oil, emulsion, gel emulsion, ointment, spray, suppository or stick.

20. The method according to claim 11, wherein said composition further comprises a conditioning agent selected from the group consisting of dimethicone or dimethylpolysiloxane, glycerine, almond oil, phenyl trimethicone, borage oil, malva extract and/or mucilage, panthenol, extract of calendula, ethylhexylglycerin, caprylyl glycol, aspartic acid, maltodextrins and glyceryl stearate.

21. The method according to claim 11, wherein said composition further comprises a surfactant selected from the group consisting of cetyl alcohol, cetyl (20) OE or ceteth-20, stearyl (20) OE or steareth-20 and PEG-75 stearate.

22. The method according to claim 11, wherein said composition further comprises a preservative, an antioxidant, a liquorice dry extract, a binder, a stabilizing agent or a chelating agent.

23. The method according to claim 11, wherein said composition is formulated as cream, gel cream, gel, oil, emulsion, gel emulsion, ointment, spray, suppository or stick.

* * * * *